(12) United States Patent
Le Meur et al.

(10) Patent No.: US 11,903,946 B2
(45) Date of Patent: Feb. 20, 2024

(54) TRIAZINE FORMULATIONS WITH A SECOND ACTIVE INGREDIENT AND SURFACTANT(S)

(71) Applicant: CEVA SANTE ANIMALE, Libourne (FR)

(72) Inventors: Anne-Claire Le Meur, Libourne (FR); Florence Guimberteau, Montussan (FR)

(73) Assignee: CEVA SANTE ANIMALE, Libourne (FR)

(*) Notice: Subject to any disclaimer, the term of this patent is extended or adjusted under 35 U.S.C. 154(b) by 184 days.

(21) Appl. No.: 17/494,866

(22) Filed: Oct. 6, 2021

(65) Prior Publication Data

US 2022/0023304 A1    Jan. 27, 2022

Related U.S. Application Data

(62) Division of application No. 14/650,079, filed as application No. PCT/EP2013/075760 on Dec. 6, 2013, now Pat. No. 11,331,321.

(30) Foreign Application Priority Data

Dec. 7, 2012    (EP) .................................. 12306548

(51) Int. Cl.
| | |
|---|---|
| *A61K 31/53* | (2006.01) |
| *A61J 1/20* | (2006.01) |
| *A61K 33/26* | (2006.01) |
| *A61P 33/02* | (2006.01) |
| *A61K 9/08* | (2006.01) |
| *A61K 47/02* | (2006.01) |
| *A61K 9/10* | (2006.01) |
| *A61K 45/06* | (2006.01) |
| *A61K 9/00* | (2006.01) |

(52) U.S. Cl.
CPC ............ *A61K 31/53* (2013.01); *A61J 1/2093* (2013.01); *A61K 9/0095* (2013.01); *A61K 9/08* (2013.01); *A61K 9/10* (2013.01); *A61K 33/26* (2013.01); *A61K 45/06* (2013.01); *A61K 47/02* (2013.01); *A61P 33/02* (2018.01)

(58) Field of Classification Search
None
See application file for complete search history.

(56) References Cited

U.S. PATENT DOCUMENTS

| | | | |
|---|---|---|---|
| 3,145,142 | A | 8/1964 | Lansbury |
| 4,493,826 | A | 1/1985 | Strayer |
| 7,655,597 | B1 | 2/2010 | Sanders |
| 7,915,257 | B2 | 3/2011 | Greif et al. |
| 11,331,321 | B2 | 5/2022 | Le Meur et al. |
| 2005/0201967 | A1 | 9/2005 | Albrecht et al. |
| 2005/0266005 | A1 | 12/2005 | Heavner et al. |
| 2010/0179151 | A1 | 7/2010 | Heep et al. |
| 2015/0313905 | A1* | 11/2015 | Karembe ............. A61K 9/0019 514/25 |
| 2022/0023305 | A1 | 1/2022 | Le Meur et al. |
| 2022/0265665 | A1 | 8/2022 | Le Meur et al. |

FOREIGN PATENT DOCUMENTS

| | | |
|---|---|---|
| BR | PI0812172 | 12/2008 |
| CA | 2688613 | 12/2008 |
| CN | 101553208 A | 10/2009 |
| CN | 101 678 031 | 3/2010 |
| CN | 101 904 858 | 12/2010 |
| CN | 102 000 100 | 4/2011 |
| DE | 10 2007 025908 | 12/2008 |
| JP | 2010-528996 | 8/2010 |
| WO | WO 01/26660 | 4/2001 |
| WO | WO 02/069911 | 9/2002 |
| WO | WO 2008/048018 | 4/2008 |
| WO | WO 2014/086958 | 6/2014 |
| WO | WO 2014/086959 | 6/2014 |

OTHER PUBLICATIONS

Gadhave, Determination of Hydrophilic-Lipophilic Balance Value, International Journal of Science and Research, vol. 3, Issue 4, Apr. 2014, pp. 573-575 . (Year: 2014).*

Anonymous, "Sunscreen compositions comprising colour pigments," *IP.com Journal*, IP.com, West Henrietta, NY, May 21, 2008, pp. 1-42.

Database WPI, Week 201128, Thomson Scientific, London, GB; AN 2011-A32770, XP002696742, p. 1.

Database WPI, Week 201153, Thomson Scientific, London, GB; AN 2011-F22109, XP002696743, pp. 1-2.

Kaushik, D. et al. "Design & synthesis of 2-(substituted aryloxy)-5-(substituted benzylidene)-3-phenyl-2,5-dihydro-1H-[1,2,4] triazin-6-one as potential anticonvulsant agents" *European Journal of Medical Chemistry*, 2010, pp. 3960-3969, vol. 45.

Ma, X. et al. "Synthesis and in vitro evaluation of 2,4-diamino-1,3,5-triazine derivatives as neuronal voltage-gated sodium channel blockers" *Bioorganic & Medicinal Chemistry Letters*, 2009, pp. 5644-5647, vol. 19.

Bos, J. D. et al. "The 500 Dalton rule for the skin penetration of chemical compounds and drugs" *Experimental Dermatology*, 2000, pp. 165-169, vol. 9.

(Continued)

*Primary Examiner* — David J Blanchard
*Assistant Examiner* — Sarah J Chickos
(74) *Attorney, Agent, or Firm* — SALIWANCHIK, LLOYD & EISENSCHENK

(57) ABSTRACT

The present invention is related to novel compositions comprising at least one active ingredient of the family of the triazines combined with another active ingredient and specific compounds that allow the reduction of foam formation. More particularly, the invention relates to compositions in the form of aqueous suspensions comprising a triazine, an iron complex, and one or more surfactant(s) having a particular HLB.

27 Claims, 1 Drawing Sheet

(56) References Cited

OTHER PUBLICATIONS

Anonymous, "Emulsions and the HLB System" *Convergent Cosmetics*, Feb. 18, 2009, pp. 1-19, XP007907287, Retrieved from the Internet: URL:http://web.archive.org/web/20051014095945/http://home.earthlink.net/~skinesscentuals/HLBSystem.pdf.
Anonymous, "Simethicone Emulsion" *Interim Revision Announcement*, Jan. 1, 2014, pp. 1-2, Retrieved from the Internet: URL:https://web.archive.org/web/20131203014932if_/http://www.usp.org/sites/default/files/usp_pdf/EN/simethicone_emulsion.pdf.
Anonymous, "Hydrophilic-lipophilic balance" Wikipedia, last edited May 6, 2018, obtained Sep. 10, 2018, pp. 1-3.
Anonymous, "Baycox 50 mg/ml oral suspension, pig. Summary of Product Characteristics" Irish Medicines Board, Nov. 25, 2011, pp. 1-4.
Colas, A. et al. "Silicones in Pharmaceutical Applications. Part 4: Silicone Antifoams and Silanes" 2006, pp. 1-5.
https://www.animalwised.com/coccidiosis-in-birds-symptoms-treatment-and-prevention-357.html, 2018, pp. 1-9.

\* cited by examiner

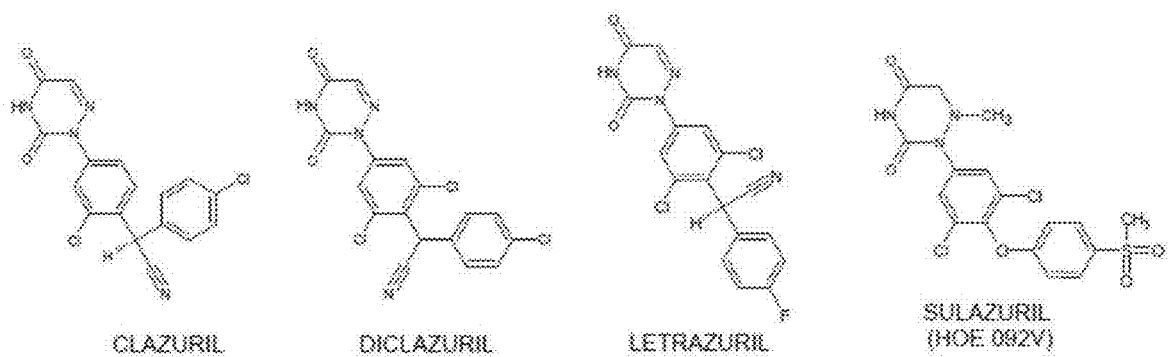
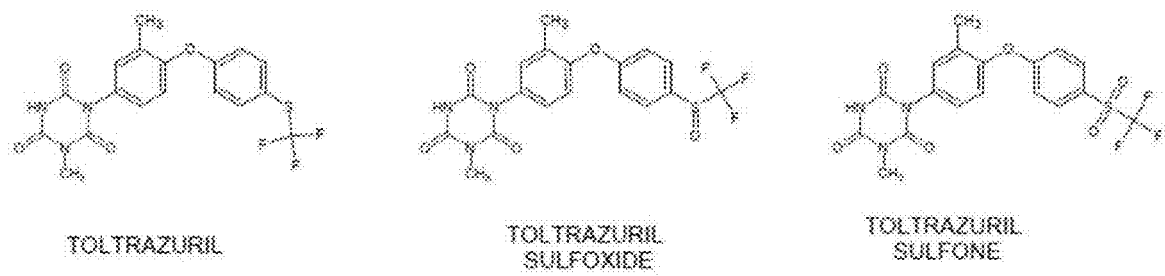

TRIAZINE FORMULATIONS WITH A SECOND ACTIVE INGREDIENT AND SURFACTANT(S)

CROSS-REFERENCE TO RELATED APPLICATIONS

This application is a divisional of U.S. application Ser. No. 14/650,079, filed Jun. 5, 2015, which is the U.S. national stage application of International Patent Application No. PCT/EP2013/075760, filed Dec. 6, 2013.

The present invention is relative to triazine formulations and the uses thereof. The invention more particularly relates to new aqueous suspensions of a triazine comprising one or more surfactant(s) having a particular HLB (Hydrophilic-Lipophilic Balance). The invention also relates to compositions comprising at least one triazine, preferably toltrazuril, and a further active ingredient (e.g., an antibiotic, anti-inflammatory agent, anthelmintic, endectocide, mineral or vitamin). The compositions preferably comprise one or more surfactant(s) having an HLB (Hydrophilic-Lipophilic Balance) comprised between 1 and 8. The compositions are adapted for parenteral and/or oral administration. The invention also relates to kits and methods of preparing such compositions, as well as the uses thereof in non-human animals such a porcine, an ovine, a bovine, a canine, a feline or an avian for protecting against infectious diseases, such as protozoal disorders.

BACKGROUND OF THE INVENTION

Triazines are commonly used in the veterinary industry to treat non-human animals against a variety of diseases. Triazines are broad-spectrum antimicrobials that inhibit both gram-positive and gram-negative bacteria, as well as some protozoa, such as coccidia.

Triazines, such as toltrazuril and ponazuril, are authorized agents for the treatment and control of coccidioses, which are frequent parasitic infectious diseases caused by protozoans such as *Eimeria* or *Isospora*. Triazines are also effective against other protozoal parasites, e.g., *toxoplasma*, *cryptosporidia*, and *sarcocystis*. They are essentially administered to the animals by oral route. In this regard, EP116175 refers to a water-miscible solution of a triazine for oral administration, DE19603954 proposes triazine granules for oral administration, DE19824483 relates to semi-solid preparations which are applied orally, and EP2164496 relates to triazine-iron combination products. The triazine compound is administered orally, as a suspension.

WO 01/26660 and U.S. Pat. No. 6,465,460 relate to a sodium salt of triazine compounds and to compositions for oral or parenteral administration. According to this patent the sodium salt allows the use of lower doses of the compound. Although different administration routes are mentioned, all of the experimental section is limited to intravenous and oral administration. Furthermore, the patent indicates that several administrations and/or a sustained release dose are required for maintaining appropriate blood levels. In particular, the patent proposes a starting dose and several maintenance doses, which need to be administered over several days.

Despite preliminary investigations on (e.g., transdermal), oral administration is still preferred today because it is believed to provide the most appropriate pharmacokinetic profile of the drug, especially in young non-human animals. In particular, while the oral formulation requires substantive manipulation and cannot provide strict dosage control, it is believed to ensure appropriate bioavailability and therapeutic efficacy of the triazine compounds.

Oral administration may, however, present drawbacks. Indeed, oral administration cannot be conveniently combined with other treatments which are given by injection (e.g., antibiotics, anti-inflammatory agents, anthelmintics, endectocides, minerals or vitamins) at early stages of growth of the non-human animals and therefore involves additional manipulation of the non-human animals. Oral administration may also prevents strict control of the dosage administered to each non-human animal.

It has been proposed in the art to combine a triazine with iron, in order to treat both coccidiosis and anemia in piglets. However, such a combination raises formulation and administration problems. Indeed, the triazine is usually administered orally, while the iron compound is typically injected. EP2164196 proposes oral compositions of both agents but, at the same time, recognizes that iron compounds administered orally exhibit low bioavailability and should be administered within 8 to 10 hours after birth, leading to a separate schedule of administration for both compounds. Moreover, it has been disclosed that depending on the dosage or formulation, iron compounds administered by injection may cause side effects.

Accordingly, there is a need in the art for optimized triazine formulations/administration protocols, especially for optimized triazine/iron formulations that are efficient and convenient. Such optimized formulations should preferably contain a triazine (e.g., toltrazuril) and an iron complex in the same formulation, suitable for combined administration, with dosages, amounts, and pharmacokinetics adapted to provide effective protection of non-human animals, even shortly after birth.

The present invention solves the above technical problems by providing novel triazine formulations in the form of stable aqueous suspensions with antifoaming properties, which fulfill the conditions for pharmaceutical use and which are adapted for oral and parenteral administration.

SUMMARY OF THE INVENTION

An object of the invention resides in a composition comprising a triazine compound, wherein said composition is an aqueous suspension and comprises one or more surfactant(s) having an HLB (Hydrophilic-Lipophilic Balance) comprised between 1 and 8.

Another object of the invention resides in a composition comprising at least one triazine compound and another active ingredient (preferably selected from, e.g., antibiotics, anti-inflammatory agents, anthelmintics, endectocides, minerals or vitamins), wherein said composition is an aqueous suspension containing at least one surfactant.

Another object of the invention resides in a composition comprising at least one triazine compound and another active ingredient (preferably selected from, e.g., antibiotics, anti-inflammatory agents, anthelmintics, endectocides, minerals or vitamins), wherein said composition is an aqueous suspension containing one or more surfactant(s) having an HLB comprised between 1 and 8.

The compositions of the invention may optionally further comprise at least one hydrophilic solvent and/or one or several additional surfactant(s) and/or one or several acceptable excipients or carriers. The compositions are preferably adapted for oral or parenteral administration, preferably for injection such as subcutaneous, intramuscular, intradermal or intravenous injection.

A preferred triazine compound is a triazinetrione and, more preferably, toltrazuril. The further active ingredient may be selected, preferably, from antibiotics, anthelmintics, endectocides, anti-inflammatory agents, vitamins and/or minerals. Preferably, the further active ingredient is an iron complex such as, without limitation, iron dextran, iron dextran glucoheptonic acid, iron isomaltoside and iron carboxymaltose complexes. Even more preferably, the iron complex includes an aqueous colloidal solution of beta-ferric oxyhydroxide and dextran glucoheptonic acid (glepto-ferron, commercialized under the trademark Gleptosil® or Ursoferran®).

A preferred object of the invention resides in a composition in the form of an aqueous suspension comprising (i) a triazine compound, (ii) an iron complex, and (iii) one or more surfactant(s) having an HLB comprised between 1 and 8.

Preferred surfactants having an HLB comprised between 1 and 8 include, without limitation, soybean lecithins, sorbitan esters, polyol esters, silicon emulsions, simethicone emulsions, propylene glycol monolaurate, propylene glycol monocaprylate, glyceryl monooleate, phospholipids, lauroyl polyoxylglycerides, linoleoyl polyoxylglycerides, oleoyl polyoxylglycerides, or polyoxyethylene alkyl ether. Most preferred surfactants are sorbitan monooleate, propylene glycol monolaurate and simethicone emulsion.

Preferred hydrophilic solvents are semi-polar to polar hydrophilic solvents such as, without limitation, diethylene glycol monoethyl ether (Transcutol®), glycerol, polyethlene glycol and propylene glycol.

The compositions of the invention may be prepared or stored in various containers, preferably glass or plastic containers. The plastic containers are preferably made of materials such as, without limitation, polypropylene, polyethylene, high-density polyethylene (HDPE), polyethylene terephthalate, polyvinyl chloride, polyethylene-vinyl acetate, polyolefins, polyesters, polyamide, or polymers. Typically, the compositions of the invention are stored in a bottle or flask. In a specific embodiment, the compositions of the invention are stored in a multi-layered plastic polymeric container comprising at least one polyolefin.

Another object of the invention is a kit comprising a container, preferably a bottle or flask, comprising a composition as defined above, and a notice. The container typically comprises all of the ingredients in admixture. Alternatively, in a particular embodiment, the container comprises two (or more) separated compartments, each comprising distinct ingredient(s) of the composition, which are typically mixed prior to administration.

Another object of the invention is a kit comprising two containers, a first container comprising the triazine compound, for instance as a powder, and a second container comprising the other ingredient in an aqueous suspension with one or more surfactant(s) having an HLB comprised between 1 and 8. The contents of the two containers are typically mixed prior to administration.

Another object of the invention relates to a method for preparing a composition as defined above, comprising providing a triazine, a further active ingredient, and a surfactant having an HLB comprised between 1 and 8, and mixing said ingredients, generally in an appropriate vehicle or carrier. Typically, the method comprises (i) providing a triazine compound, preferably in the form of a powder, (ii) providing the further active ingredient in an aqueous suspension with one or more surfactant(s) having an HLB comprised between 1 and 8, and (iii) mixing said ingredients in an appropriate container. The compositions of the invention may be prepared in advance and stored in any appropriate container (flask, bottle, etc.). Alternatively, the compositions may be prepared extemporaneously, e.g., by mixing the ingredients shortly before administration.

A further object of the invention is a composition or kit as defined above for use to treat (e.g., prevent, retard, protect against, reduce or cure) an infectious disease in a non-human animal, preferably a parasitic infectious disease caused by a protozoan.

A further object of the invention relates to a method for treating (e.g., preventing, retarding, protecting against, reducing, or curing) an infectious disease in a non-human animal, preferably a parasitic infectious disease caused by a protozoan, comprising the administration of an effective amount of a composition as defined above to the non-human animal. Administration may be a single administration. Alternatively, repeated administration may be performed. As indicated above, the composition may be contained in a single container, or in two (or more) containers which are mixed extemporaneously, for instance shortly prior to administration.

The invention is particularly suited for protecting porcine, ovine, bovine, canine, feline, or avian against parasitic infectious diseases caused by protozoans. It is particularly well adapted for the treatment of young non-human mammals such as a bovine or a swine and more preferably a piglet newborn to 10 days old, preferably newborn to 3 days old, more preferably newborn to 48 hours old.

LEGEND TO THE FIGURES

FIG. 1: Structure of preferred triazine compounds.

DETAILED DESCRIPTION OF THE INVENTION

The present invention provides novel formulations comprising at least one molecule of the triazine family and, preferably, another active ingredient which is in the form of an aqueous suspension, does not foam and is suitable for treating parasitic infectious diseases caused by protozoans. More specifically, the invention provides a composition of triazine(s) and another active ingredient such as an iron complex and a surfactant agent characterized by an HLB (Hydrophilic-Lipophilic Balance) comprised between 1 and 8.

The invention indeed proposes to formulate triazines and another active ingredient (e.g., antibiotics, anti-inflammatory agents, anthelmintics, endectocides, minerals or vitamins) as aqueous suspensions, which provide efficient pharmacokinetic profile. Suspensions are dispersions of the active principle(s) solid particles (insoluble or practically insoluble) in a liquid medium. Usually, the size of solid particles varies from one or a few nanometers to 50 micrometers. It is thus a heterogeneous mixture made up of an external continuous liquid phase and an internal solid phase. The use of pharmaceutical or veterinary compositions in the form of aqueous suspensions has numerous advantages; for example, the absorption of active ingredients comprised in a suspension form is generally faster compared to a solid form (a tablet, for example) and the chemical stability of certain active ingredients is improved with a suspension, compared to a solution. However, suspensions are difficult to prepare because factors which control the physical stability of the suspensions are numerous. Generally, the crystals of active ingredient do not have the same density as the continuous phase of the suspension, from where the observation of creaming or sedimentation when the suspension is left at rest. Indeed, the active particles precipitate at the end of a certain time. It is thus necessary, before use, to stir the suspension in order to disperse the particles of the active ingredient throughout the fluid phase and thus to obtain a homogeneous sample. One of the major problems of aqueous suspensions is foam formation when reconstituting liquid dosage forms after agitation or during manufacturing processes. Such a formation of foam (gas bubbles dispersed in the liquid) is highly undesirable. In this regard, aqueous suspensions containing triazines tend to form a lot of foam which, in addition to aspect problems, does not allow to guarantee an exact dosage and can possibly present risks of gas embolism if bubbles of air are injected.

The present invention shows that efficient suspensions of a triazine and another active ingredient can be prepared by adding to the composition particular surfactants, preferably surfactants with a low HLB (preferably between 1 and 8). By using appropriate surfactants according to the invention, it is possible to prepare aqueous suspensions of triazine in which foam (if formed) disappears very quickly.

The inventors have surprisingly found that the addition of a surfactant having a low HLB to an aqueous suspension of a triazine with another active ingredient such as an iron complex leads to significant foaming reduction or total foaming suppression.

The present invention thus provides aqueous suspensions of one or several triazine compound(s) and one or several further active ingredient(s) in a liquid medium containing one or more surfactant(s) with a low HLB. The compositions may in addition further comprise one or more hydrophilic solvent(s) and/or one or several additional surfactants, and/or one or several excipients or carriers.

Triazine Compounds

The term "triazine(s)" designates a well-known class of active substances, especially against infections with coccidia. Typical triazines for use in a method or composition of the invention are compounds of formula A or B below, of any purity, preferably having a purity of at least 90%, as well as any salt, ester, racemate, isomer, or prodrug thereof:

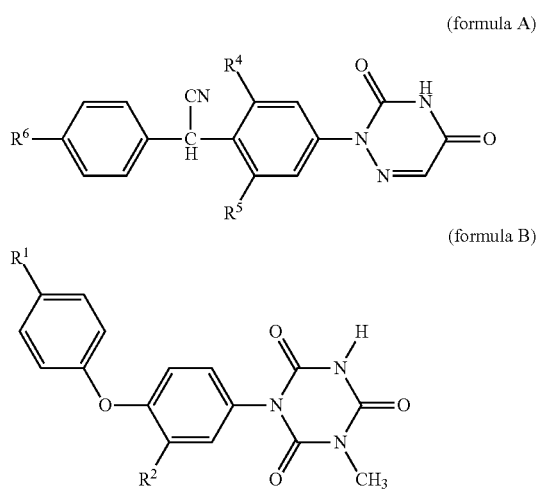

(formula A)

(formula B)

wherein
$R^1$ is $R^3$—$SO_2$— or —S—,
$R^2$ is alkyl, alkoxy, halogen or $SO_2N(CH_3)_2$,
$R^3$ is a haloalkyl,
$R^4$ and $R^5$ are independently from each other a hydrogen or Cl atom; and
$R^6$ is fluorine or chlorine.

Triazine compounds more preferably include triazinediones (formula A) and triazinetriones (formula B). Examples of triazinediones include, without limitation, clazuril ($R^4$ is Cl, $R^5$ is H, $R^6$ is Cl in formula A), diclazuril ($R^4$ is Cl, $R^5$ is Cl, $R^6$ is Cl in formula A) or letrazuril ($R^4$ is Cl, $R^5$ is Cl, $R^6$ is F in formula A). Preferred 1,2,4-triazinediones are diclazuril and sulazuril.

Triazines for use in the present invention are, more preferably, triazinetriones of formula B, even more preferably wherein $R^2$ is a C1 to C4 alkyl or alkoxy group (e.g., methyl, ethyl, or n-propyl) and/or $R^3$ is a C1 to C3 perfluoroalkyl group (e.g., trifluoromethyl).

Specific and most preferred triazines of the invention are toltrazuril ($R^1$=$R^3$—S—, $R^2$=$CH_3$, $R^3$=$CF_3$ in formula B) and ponazuril ($R^1$=$R^3$—$SO_2$—, $R^2$=$CH_3$, $R^3$=$CF_3$ in formula B).

Toltrazuril (1-methyl-3-[3-methyl-4-[4-(trifluoromethyl)tio)phenoxyl]phenyl]-1,3,5-triazine(1H,3H,5H)-2,4,6-trione) is widely used in porcines, ovines, bovines and avians for the prevention and treatment of coccidiosis by oral administration. It is currently available on the market as Cevazuril® or Baycox®. Methods for the preparation of toltrazuril are disclosed in various patents such as U.S. Pat. Nos. 4,219,552, 5,219,853, EP0201030, and EP0879057. The chemical structure of toltrazuril is represented in formula (C) below:

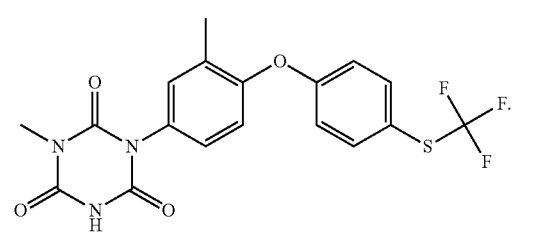

(Formula C)

The chemical structures of further examples of triazine compounds for use in the present invention are depicted in FIG. 1.

The triazine(s) are present in the composition of the invention preferably in an amount from 1% to 10% by weight of the total weight of the composition. Preferentially, the compositions contain from 1% to 6% of one or more triazine compound(s), and even more preferentially from 2% to 5% of one or several triazine compound(s). The compositions preferably contain only one triazine. The most preferred triazine compound according to the invention is toltrazuril, the percentage of which in the composition of the invention is comprised between 1% and 6% by weight, and even more preferably between 2 and 5%.

The triazine(s) as defined is the present invention comprise(s) their salts, such as sodium salts.

Other Active Ingredient(s)

As indicated above, the compositions of the invention preferably combine a triazine and another active agent, which may be selected preferably from antibiotics, anti-inflammatory agents, anthelmintics, endectocides, minerals or vitamins.

Antibacterial antibiotics are commonly classified based on their mechanism of action, chemical structure, or spectrum of activity. Most target bacterial functions or growth processes. Those that target the bacterial cell wall (penicillins and cephalosporins) or cell membrane (polymixins), or interfere with essential bacterial enzymes (rifamycins, lipiarmycins, quinolones, and sulfonamides), have bactericidal activities. Those that target protein synthesis (aminoglycosides, macrolides, and tetracyclines) are usually bacteriostatic. Further categorization is based on their target specificity. "Narrow-spectrum" antibacterial antibiotics target specific types of bacteria, such as gram-negative or gram-positive bacteria, whereas broad-spectrum antibiotics affect a wide range of bacteria. Following a 40-year hiatus in discovering new classes of antibacterial compounds, four new classes of antibacterial antibiotics have been brought into clinical use: cyclic lipopeptides (such as daptomycin), glycylcyclines (such as tigecycline), oxazolidinones (such as linezolid) and lipiarmycins (such as fidaxomicin). Preferred antibiotics are aminoglycosides such as neomycin, beta-lactam antibiotics such as ampicillin and amoxicillin, macrolides such as spiramycin and tylosin, polymixins such as colistin and the family of chloramphenicol, such as chloramphenicol, thiamphenicol and florfenicol.

Anti-inflammatory agents refer to the property of a substance or treatment that reduces inflammation, for example but not limited to steroids (e.g., glucocorticoids, corticosteroids), non-steroidal anti-inflammatory drugs (NSAIDs) or immune-selective anti-inflammatory derivatives (ImSAIDs).

Anthelmintics are drugs that are used to treat infections with parasitic worms. This includes both flatworms, e.g., flukes and tapeworms, and roundworms, i.e., nematodes. They are separated into classes on the basis of similar chemical structure and mode of action, such as but not limited to piperazine, flubendazole, benzimidazole, oxybendazole, nicotinic receptor agonists (levamisole, pyrantel and morantel), oxindole alkaloid (paraherquamide A and marcfortine A), macrocyclic lactones and milbemycins, cyclodepsipeptide molecules (emodepside) and pyruvate ferredoxin oxidoreductase inhibitors (nitazoxanide).

Endectocides are used in the treatment and control of internal (endo-) and external (ecto-) parasites in certain animals. Endectocides comprise two groups of closely related compounds: the avermectins, such as but not limited to doramectin, eprinomectin, and ivermectin, and the milbemycins, such as but not limited to moxidectin.

Vitamins are organic compounds required by an animal as a vital nutrient in limited amounts, such as but not limited to Vitamin A, Vitamins B1 to B12, Vitamin C, etc.

Minerals are trace elements, micronutrients or ions, such as but not limited to calcium, copper, magnesium, selenium or iron. Generally minerals are elements known by a skilled person in the veterinary field according to the needs of each non-human animal treated. A preferred mineral for use in the invention is an iron complex.

Iron Complexes

Because iron salts may be toxic at high concentrations, the iron is preferably complexed to a macromolecule, such as a carbohydrate or polymer. For example we can cite iron dextran, glucoheptonic acid of iron dextran, iron isomaltoside, iron carboxymaltose iron-sucrose, iron-oligosaccharide and iron-gluconate compounds. Examples of other preferred iron complexes include, without limitation, an aqueous colloidal solution of beta-ferric oxyhydroxide (or ferric hydroxide) and dextran glucoheptonic acid (gleptoferron, commercialized under the trademark Gleptosil® or Ursoferran®) or a ferric hydroxide with a low-molecular-weight dextran (commercialized under the trademark Uniferon® or Dexafer®) or a ferric hydroxide with macromolecular dextran (commercialized under the trademark Ferroforte®) or a ferric compound of type I.

The iron (as complex) represents preferably from 10% to 25% by weight of the total weight of the composition. Preferentially, the compositions of the invention contain from 10% to 20% of iron (as complex(es)), and even more preferentially from 12% to 20% of iron (as complex(es)). The most preferred iron complex for use in the invention is a colloidal solution of beta-ferric oxyhydroxide (or ferric hydroxide) and dextran glucoheptonic acid (gleptoferron). The percentage of iron (as complex) in the compositions of the invention may be comprised between 12% and 20% by weight. Advantageously, the iron complex used may contain an effective amount of promoters of non-heme iron absorption, such as but not limited to vitamin C (ascorbic acid), derivatives of ascorbic acid such as ascorbyl palmitate, or an ester synthetic compound of palmitic acid with L ascorbic acid (vitamin C palmitate or erythorbic acid).

Surfactants

The term "surfactant" designates an agent which modifies a liquid's surface tension, in particular that of water.

Preferred surfactants of the invention are surfactants having a low HLB (Hydrophilic-Lipophilic Balance), more preferably a HLB ranging from 1 to 8. The invention shows that such particular class of surfactants allows the formation of suspensions of a triazine and another active ingredient which do not form foam upon stirring or in which foam (if formed) disappears very quickly.

A surfactant molecule can be described as a hydrophobic chain (affinity for nonpolar solvents) linked to a hydrophilic chain (affinity for polar solvents). Consequently, surfactants present antagonistic properties and, once formulated in water, the hydrophobic part rejects the molecule on the surface and the hydrophilic part tends to plunge within the liquid.

The HLB is used to determine the hydrophilic or hydrophobic dominant character of a surfactant. HLB values have been proposed in 1949 by Griffin (Griffin, W. C., Surface-Active Classification of Agents by HLB, Newspaper of the Society of Cosmetic Chemists, 1949, 1:31). This method allows the determination of reference points which quantify the existing balance between the hydrophilic part and the lipophilic part of the molecules of the surfactant, and which are related to its solubility in water. The scale varies from 0 to 40: the higher the value of the HLB, the greater its solubility in water.

In 1957, Davies suggested a method based on calculating a value based on the chemical groups of the molecule. The advantage of this method is that it takes into account the effect of stronger and weaker hydrophilic groups. According to the method of Davies:

$$HLB = \Sigma HLB_{groupes\ hydrophiles} - \Sigma HLB_{groupes\ hydrophobes} + 7.$$

Preferred surfactants of the invention are hydrophobic with a low HLB, more preferably ranging from 1 to 8, typically of 1, 2, 3, 4, 5, 6, 7, or 8. The surfactants for use in the compositions of the invention are selected from, but not limited to, soybean lecithins, sorbitan esters, polyol esters, silicone emulsion, simethicone emulsion, propylene glycol monolaurate, propylene glycol monocaprylate, glyceryl monooleate, phospholipids, lauroyl polyoxylglycerides, linoleoyl polyoxylglycerides, oleoyl polyoxylglycerides, or polyoxyethylene alkyl ether. The most preferred surfactants are sorbitan monooleate, propylene glycol monolaurate and simethicone emulsion.

In a particular embodiment, the preferred surfactant is a simethicone emulsion, which typically comprises about 25 to 35% of simethicone USP by weight. In a specific example, the simethicone emulsion contains the following constituents: polydimethylsiloxane, octamethylcyclotetrasiloxane, methylcellulose, decamethylcyclopentasiloxane, methylated silica and sorbic acid.

The surfactant(s) are preferably present in the composition in a total amount of 0.01 to 5% by weight of the total weight of the composition. Preferentially, the composition contains from 0.05 to 3% of surfactant with a low HLB, and even more preferentially from 0.05 to 1%.

The surfactants of the invention are efficient at preventing foaming by lowering surface tension and cohesive binding of the liquid phase. They are also compatible with triazines and another active ingredient, and can make for stable aqueous suspensions which are particularly adapted.

In this regard, another object of the invention resides in the use of a surfactant having an HLB between 1 and 8 to prevent foaming in a triazine and iron complex aqueous suspension.

Another object of the invention resides in a method for reducing foaming in an aqueous triazine suspension with another active ingredient, preferably an iron complex, comprising adding to the suspension an effective amount of a surfactant having an HLB between 1 and 8.

The terms "prevent foaming" and "reduce foaming" designate aqueous suspensions which do not form foam upon stirring or in which foam (if formed) disappears very quickly.

Optional High HLB Surfactants

In particular embodiments, in addition to the low HLB surfactant as defined above, the compositions of the invention also contain a further surfactant, particularly a high HLB surfactant. The addition of such a high HLB surfactant in the suspension can further improve triazine incorporation into the final formulation. A high HLB surfactant is a surfactant having an HLB strictly superior to 8.

Preferred high HLB surfactants are selected from, but not limited to, polyethylene castor oil derivatives, polyoxyethylene alkyl ether, polyoxyethylene sorbitan fatty acid esters, polyoxyethylene stearate, sodium lauryl sulfate, sodium docusate, cetrimide, phospholipids, or cetylpyridinium chloride.

Usually, high HLB surfactant(s) constitute(s) from 0% to 5% by weight of the total weight of the composition. Preferentially, when present, the high HLB surfactant(s) represent(s) from 0.05% to 5% of the composition, preferably from 0.05% to 1%.

Solvents

The composition according to the invention may optionally comprise one or more additional hydrophilic solvents. The hydrophilic co-solvents are used, e.g., in order to reduce the time of wetting and the time of dispersal of the aqueous suspension.

Preferred solvents are hydrophilic semi-polar to polar solvents. The solvents are preferentially selected from, but not limited to, diethylene glycol monoethyl ether, glycerol, polyethlene glycol and propylene glycol.

Usually, the hydrophilic solvent(s) constitute(s) from 0% to 30% by weight of the total weight of the composition. Preferentially, when present, the solvent(s) represent(s) from 1% to 30% of the composition, preferably from 1 to 20%, even more preferentially from 1% to 15%.

Salts

The composition according to the invention may optionally comprise one or several salts. Salts are used in order to complete surfactant efficiency.

Preferred salts are selected from, but are not limited to, calcium gluconate, calcium phosphate, calcium chloride, calcium sulfate, calcium carbonate, magnesium gluconate, magnesium phosphate, magnesium chloride, magnesium sulfate, magnesium carbonate, potassium phosphate, potassium gluconate, potassium chloride, potassium sulfate, potassium carbonate, sodium gluconate, sodium chloride, sodium carbonate, sodium phosphate, sodium citrate, sodium sulfate, ammonium chloride, or ammonium carbonate.

Usually, salt(s) represent(s) from 0% to 10% by weight of the total weight of the composition. Preferentially, when present, the salt(s) represent(s) from 0.1% to 10% of the composition, preferably from 0.5% to 4%, even more preferentially from 0.5% to 2%.

Preservatives

The composition according to the invention may optionally comprise one or several preservatives. Preferred preservatives are selected from, but not limited to, ethanol, benzoic acid and the sodium or potassium salts thereof, chlorobutanol, benzyl alcohol, phenylethanol, methyl, ethyl, propyl or butyl p-hydroxybenzoates, phenol, m-cresol, p-chloro-m-cresol or benzalkonium chloride.

Usually, preservatives represent from 0% to 10% by weight of the composition. Preferentially, when present, the preservative(s) represent(s) from 0.05% to 5%, preferably from 0.1% to 3%.

Thickeners

The composition according to the invention may optionally comprise one or several thickeners. Preferred thickeners are selected from, but not limited to, octyldecanol, aluminium monostearate, calcium phosphate, sodium phosphate, chitosan, dextran, glyceryl behenate, glyceryl monoleate, glyceryl monostearate, colloidal silicon dioxide, cellulose and its derivatives, starch, propylene carbonate, hydroxypropyl methylcellulose, polyvinylpyrrolidone, sorbitol, trehalose or sucrose.

Usually, thickeners represent from 0% to 10% by weight of the composition. Preferentially, when present, the thickener(s) represent(s) from 0.05% to 5%, preferably from 0.05% to 2%.

Preferred Compositions of the Invention

The present invention provides optimized combined compositions comprising a triazine with another active ingredient, both suspended in an aqueous medium containing one or more specific surfactants. Furthermore, the invention provides optimal dosages and administration routes for all the compounds, in order to confer the best protective effect during the treatment procedures.

Preferred compositions of the invention comprise one triazine and one iron complex, which may be combined with one or several, preferably one, surfactant having a low HLB. The most preferred compositions comprise a further hydrophilic solvent.

A particular object of the invention resides in an oral or injectable composition comprising:
  from 1% to 10% by weight of a triazine, preferably a triazinetrione, more preferably toltrazuril;
  from 10% to 25% by weight of an iron (as a complex, preferably gleptoferron);
  from 0.01% to 5% by weight of one or several surfactant(s), preferably sorbitan monooleate, propylene glycol monolaurate or a simethicone emulsion;

from 0% to 30% by weight of one or several hydrophilic solvent(s);
from 0% to 10% by weight of one or several salt(s); and
from 0% to 5% by weight of one or several high HLB surfactant(s).

In a particular embodiment, the composition further comprises:
from 0% to 10% by weight of one or several thickening agent(s), and
from 0% to 10% by weight of one or several preservative(s).

The above weight % are provided with reference to the total weight of the composition.

Another particular object of the invention resides in an oral or injectable composition comprising:
from 1% to 6% by weight of a triazine, preferably a triazinetrione, more preferably toltrazuril;
from 10% to 20% by weight of an iron (as a complex, preferably gleptoferron);
from 0.05% to 3% by weight of one or several surfactant(s), preferably selected sorbitan monooleate, propylene glycol monolaurate or a simethicone emulsion;
from 0% to 20% by weight of one or several hydrophilic solvent(s), typically from 1% to 20%;
from 0% to 4% by weight of one or several salt(s), typically from 0.5% to 4%;
from 0% to 4% by weight of high HLB surfactant, typically from 0.05% to 4%;
from 0% to 5% by weight of one or several thickening agent(s), typically from 0.05% to 5%; and
from 0% to 5% by weight of one or several preservative(s).

The above weight % are provided with reference to the total weight of the composition.

In another further preferred embodiment, the composition according to the invention is an aqueous suspension comprising:
from 2% to 5% by weight of toltrazuril;
from 12% to 20% by weight of an iron complex (as gleptoferron);
from 0.05% to 1% by weight of one or several surfactant(s), preferably selected from sorbitan monooleate, propylene glycol monolaurate or a simethicone emulsion;
optionally from 1% to 15% by weight of one or several hydrophilic solvent(s);
from 0% to 2% by weight of one or several salt(s);
from 0% to 2% by weight of high HLB surfactant;
from 0% to 2% by weight of one or several thickening agent(s); and
from 0% to 3% by weight of one or several preservative(s).

The above weight % are provided with reference to the total weight of the composition.

A specific example of a composition of the invention comprises 2.9% toltrazuril, 18.8% of iron (as gleptoferron), 0.3% of sorbitan monooleate, 0.1% of copolymer Polyoxyl 35—hydrogenated castor oil, 1.5% of sodium chloride and water.

Another specific example of a composition of the invention comprises 4.2% of toltrazuril, 13.5% of iron (as gleptoferron), 0.3% of sorbitan monooleate, 0.1% of copolymer Polyoxyl 35—hydrogenated castor oil, 1.5% of sodium chloride and water.

Another more specific example of a composition of the invention comprises 4.2% of toltrazuril, 13.5% of iron (as gleptoferron), 1% of sodium chloride, 1% of polyvinylpyrrolidone, 0.6% of phenol, 0.5% of colloidal silicon dioxide, 0.1% of sodium docusate, 0.1% of a simethicone emulsion and water.

Further specific examples of preferred compositions of the invention are formulations 2-14 as disclosed in the examples.

Such compositions contain the amount of triazine and other active ingredients which are required to obtain the minimal effective dose to ensure efficient protection.

The compositions of the invention generally comprise water, qsp 100%. They may also contain additional excipients or vehicles, as will be disclosed below.

Preferred Administration Route and Excipients

The compositions of the invention are suitable for oral or parenteral administration.

In this regard, the compositions may further comprise additional veterinarily acceptable excipient(s) such as surfactants with low HLB, diluents, solvents, salts, solubilizers, adjuvants, stabilizers, surfactants with high HLB, antioxidants, preservatives, thickeners.

Powders, dispersible powders, or granules suitable for preparation of an aqueous suspension by addition of water are convenient dosage forms for oral or parenteral administration. Formulation as a suspension provides the active ingredient in a mixture with a surfactant, and, optionally, with a dispersing or wetting agent, suspending agent, and one or more preservatives.

The compositions of the invention may also be administered parenterally by injection (e.g., intramuscular, subcutaneous, intravenous, or the like), infusion or implantation in dosage forms or formulations, or via suitable delivery devices or implants containing conventional, non-toxic pharmaceutically acceptable carriers and adjuvants.

The preferred administration route of the compositions of the invention is by injection. The intramuscular administration route is most preferred.

The compositions of the invention may be administered by injection(s) using techniques and/or devices known per se in the art. In this regard, injection, such as intramuscular injection, can be performed with a syringe, a gun, a micro-needle injection device, a needle-free injection device, a pulse device, etc. In a preferred embodiment, injection is performed with a needle injector or a syringe. In another particular embodiment, injection is performed with a needle-free injection device such as a pulse needle-free system, more particularly a spring-powered, battery-powered, or compressed-gas-powered device. Specific examples of needle-free technologies are described, e.g., in WO2006/058426, WO2007/140610, or WO2009/111794. A preferred needle-free injection device for use in the present invention is the AcuShot™ needle-free technology described in the international patents WO2006/058426 and WO2007/140610.

Intramuscular injection may be made in any muscle. For livestock, such as cattle, intramuscular injection is preferably made in the area of the neck, or behind the ear, rather than in the hind limb/ham muscle or in the inguinal fold.

In this regard, a particular object of the invention resides in a use of the composition as described above in the treatment of coccidiosis in an animal, wherein said composition is administered by intramuscular injection in the neck or behind the ear for non-human mammals and in the muscles adjacent to the breastbone of adult avians.

Another particular object of the invention resides in the use of a composition as described above in the treatment of coccidiosis in avians, particularly in young avians, wherein said composition is administered by subcutaneous injection.

The compositions of the invention are more preferably administered by a single injection to the non-human animal.

The dose of triazine may vary depending on the animal species and nature of the triazine. Conventional dosage rates from 1 to 60 mg of triazine per kg bodyweight (mg/kg) of the non-human mammals may be used, preferably 5 to 50 mg/kg, and more preferably from 10 to 30 mg/kg. Illustrative dosages in the compositions of the invention are 10 mg, 20 mg, 30 mg, 40 mg, 50 mg or 60 mg toltrazuril/dose.

Within the context of the invention, the term "effective amount of" designates, preferably, a dose of the active agent which produces a clinical benefit in the treated non-human animals. Particularly, an effective amount is an amount sufficient to reduce infection or disease development, or to improve the symptoms.

Examples of preferred dosages for intramuscular toltrazuril are disclosed below for some non-human animals:
- pigs: 20 mg/kg body weight/treatment (preferably one single administration);
- cattle: 15 mg/kg body weight/treatment (preferably one single administration);
- sheep: 20 mg/kg body weight/treatment (preferably one single administration); and
- poultry: 25 mg/kg body weight/treatment (preferably one single administration).

Uses of Compositions of the Invention

The compositions of the invention may be used for the treatment of any non-human animals. The term "treatment" includes, particularly, the preventive treatment of a non-human animal against a disease. The preventive treatment of a non-human animal against a disease designates a treatment made before the non-human animal has been exposed to or in contact with the causative agent of the disease (e.g., a pathogen, virus, protozoan, cell, etc.), or after said exposure/contact but before development of the symptoms or at an early stage of development of the disease. Also, the term "preventive treatment", in relation to a population of non-human animals, designates the treatment of all members of the population even after the disease has been detected in certain members, to limit or avoid spreading to and contamination of the others. The term "treatment" or "preventive treatment" also includes the alleviation of the symptoms, as well as a delay, reduction or cure of an existing infection.

The term "treatment" also includes an increase in the welfare of the treated non-human animals, for example in increasing the production of meat, milk, wool, etc.

The invention may be used to treat (e.g., protect, prevent, delay, reduce or cure) an infectious disease in non-human animals, preferably a protozoal or microbial disease. The invention is particularly suited to treat protozoal diseases of the blood and tissues (such as babesiosis, sarcocystosis, or toxoplasmosis) or of the digestive tract (such as coccidiosis).

The invention may be used, in particular, to treat coccidiosis, particularly to prevent or protect non-human animals against coccidiosis.

In a particular embodiment, diseases which may be efficiently treated with compositions of the invention are coccidiosis and protozoal diseases, which are very frequent parasitic infectious diseases caused by coccidian protozoa such as *Eimeria, Isospora, Neospora, Sarcosporidia, cryptosporidium, Hammondia, besnoitia, hepatozoon* and *Toxoplasma*. Coccidiosis is frequent. Thus, for example, protozoans from these genera cause coccidioses and protozoal diseases all over the world.

The predominant sign of coccidiosis is diarrhea, which usually persists for 4 to 6 days. The feces may vary from white to yellow in color and from a fluid to a pasty consistency, usually without the presence of blood. Coccidiosis predisposes the non-human animal to the incidence of secondary bacterial infections and severely affected non-human animals may die.

Although the morbidity is usually high, mortality is variable, probably due to the difference in the number of oocysts ingested, differences in the environment and the presence of other co-existing disease problems. Although the disease has only a slight influence on mortality, it does influence the presence of concomitant infections and the amount of antibiotics needed to control them. The disease also drastically affects the development of non-human animals, where the daily weight gain of the infected non-human animals decreases compared to uninfected non-human animals, causing herds to have poor uniformity at weaning age. There is notable emaciation and stunting. Coccidiosis reduces growth by about 15% on average, that is, a minimum of 500 g at weaning age, and this contributes to weaning herds that are highly heterogenous.

The compositions of the invention may be used, in particular, to treat coccidiosis and protozoal diseases caused by various protozoans such as, more particularly, *Mastigophora (Flagellata), Sarcomastigophora (Rhizopoda), Myxospora, Microspora,* or *Pneumocystis carinii*. Specific examples of *Mastigophora* include *Trypanosomatidae* such as, without limitation, *Trypanosoma brucei, T. gambiense, T. rhodesiense, T. congolense, T. cruzi, T. evansi,* or *T. equinum*. Specific examples of *Sarcomastigophora (Rhizopoda)* include *Entamoebidae* and *Apicomplexa (Sporozoa)* such as *Eimeridae*, for example *E. acervulina, E. adenoides, E. alabahmensis, E. anatis, E. anseris, E. arloingi, E. ashata, E. auburnensis, E. bovis, E. brunetti, E. canis, E. chinchillae, E. clupearum, E. columbae, E. contorta, E. crandalis, E. debliecki, E. dispersa, E. ellipsoidales, E. falciformis, E. faurei, E. flavescens, E. gallopavonis, E. hagani, E. intestinalis, E. iroquoina, E. irresidua, E. labbeana, E. leucarti, E. magna, E. maxima, E. media, E. meleagridis, E. meleagrimitis, E. mitis, E. necatrix, E ninakohlyakimovae, E. ovis, E. parva, E. pavonis, E. perforans, E. phasani, E. piriformis, E. praecox, E. residua, E. scabra, E. spec., E. stiedai, E. suis, E. tenella, E. truncata, E. truttae, E. zuernii, Globidium spec., Isospora belli, L. canis, L. felis, L. ohioensis, L. rivolta, L. spec., L. suis, Neospora caninum, N. hugesi, Cystisospora spec., Toxoplasma gondii, Sarcocystis bovicanis, S. bovihominis, Leucozytozoon simondi, Plasmodium berghei, P. falciparum, P. malariae, P. ovate, P. vivax, P. spec., Babesia argentina, B. bovis, B. canis, B. spec., Theileria parva,* and *Theileria spec.*, such as *Adeleina*, for example *Hepatozoon canis* and *H. spec.*

The protozoan genera and species which in pigs lead to subclinical or clinical infections must be very especially emphasized, in particular: *Eimeria debliecki, E. suis, E. scabra, E. perminuta, E. spinosa, E. polita, E. porci, E. neodebtiecki, Isospora suis, Cryptosporidium, Toxoplasma gondii, Sarcocystis miescheriana, S. suihominis, Babesia trautmanni, B. perroncitoi,* and *Balantidium coli*. Particular examples of economically important coccidioses are infections of pigs with coccidia of the genus *Isospora* or of cattle with coccidia of the genus *Eimeria*.

The compositions according to the invention are effective against all stages of development of the pathogen.

A specific object of the invention resides in a use of the compositions as described above in treating any disease in a non-human animal, preferably a microbial disease.

Another particular object of the invention resides in a use of the compositions as described above to protect a non-human animal against coccidiosis, wherein said compositions are administered orally.

A particular object of the invention resides in a use of the compositions as described above to protect a non-human animal against coccidiosis via parenteral administration, and preferably by intramuscular or subcutaneous injection.

Storage of the Compositions of the Invention

The compositions of the invention may be provided in unit dosage forms (e.g., in single-dose ampoules), in vials containing several doses or in various containers such as bottles (in which a suitable preservative may be added). The containers (e.g., bottles) may be made of glass or of plastic, e.g., polyethylene, and preferably high-density polyethylene (HDPE). Such HDPE bottles may be, for instance, of the nominal capacity of 100 ml, 250 ml, 500 ml, 750 ml or 1000 ml, and closed respectively with polypropylene screw caps with a tamper-evident seal. Other materials and containers can also be used for storing compositions of the invention. Such containers should comply with the strict regulations and requirements for storing pharmaceutical compositions.

For example, the compositions of the invention are preferably stored in multi-layered polymeric stable containers as described in a patent application No. FR2917381. Such containers may be sterilized by irradiation with or without the composition and allow a stable conservation of said composition for a long period of time in sterile conditions. The above containers are in general formed by the association of several material layers (sheets), thereby improving the properties of the packaging, which is then particularly less rigid, less breakable, and more resistant to heat, light, gas and chemical treatments. These multi-layered containers are made of materials such as polyamides, polyolefin (PO) (polypropylene (PP), polyethylene (PE), polyethylene terephthalate (PET), polyvinyl chloride (PVC), poly(ethylenevinyl acetate) which is associated with a gas barrier layer made of ethylene vinyl acetate copolymer (copolymer EVOH), ethyl vinyl acetate (EVA), and polyamides, in order to yield an increased barrier protection against oxygen and water vapor and limit any possible alteration of the pharmaceutical composition. In a specific embodiment, the compositions of the invention are stored in a multi-layered plastic polymeric containers comprising at least one polyolefin as described in patent application No. FR2917381.

Some compositions, such as injectable compositions, may require to be sterilized before administration. These compositions are thus in general manufactured and stored in sterile conditions. The container may be sterilized either empty or filled with a composition. Alternatively, the container and the composition may be sterilized separately, and the container may then be filled in sterile conditions according to well-known methods in the art.

The containers for storing compositions of the invention preferably maintain properties of resistance after sterilization, as well as stability, mechanical resistance, transparency, and impermeability towards environmental factors, chemical products or various treatments, the reference being the glass material.

The material for the packaging or container should be pharmaceutically/veterinarily acceptable and should therefore not alter the quality of the pharmaceutical compositions. Also, preferably, the compositions should not alter the nature and composition of the container or packaging in contact therewith. Such alterations may result in the migration of chemicals from and to the packaging or container and the composition. Such chemicals may be impurities, degradation products that appear over time under the action of oxygen, light and temperature, or due to processing of the container or packaging, such as the sterilization process by irradiation. These interactions may alter over time the chemical properties of the composition, such as the stability of the active ingredient and/or of the container or packaging, or the transparency and/or color of the composition or container, thereby reducing the lifetime of the container or packaging. Furthermore, such interactions may modify the sterility, safety and efficacy of the composition.

The container may contain all of the ingredients of the compositions in admixture. In particular, the container (e.g., flask, bottle, etc.) can comprise, in suspension, the triazine compound, the further active agent(s) the surfactant(s) and, when present, the solvent(s) and/or excipient(s).

Alternatively, the ingredients may be formulated in separate containers, or in separate compartments of a same container. In this regard, in a particular embodiment, the invention uses two containers, a first container comprising the triazine compound, for instance as a powder, and a second container comprising the other ingredient(s) in an aqueous suspension with one or more surfactant(s) having an HLB comprised between 1 and 8. The content of the two containers are typically mixed prior to administration.

In another particular embodiment, the invention uses one container comprising a first and a second compartment, said compartments being separated from each other, for instance, by a membrane or wall, a first compartment comprising the triazine compound, for instance as a powder, and a second compartment comprising the other ingredient(s) in an aqueous suspension with one or more surfactant(s) having an HLB comprised between 1 and 8. The contents of the two compartments are typically mixed prior to administration, for instance by breaking or removing the separating membrane or wall.

Another object of the invention relates to a method for preparing a composition as defined above, comprising providing a triazine, a further active ingredient, and a surfactant having an HLB comprised between 1 and 8, and mixing said ingredients, generally in an appropriate vehicle or carrier. Typically, the method comprises (i) providing a triazine compound, preferably in the form of a powder, (ii) providing the further active ingredient in an aqueous suspension with one or more surfactant(s) having an HLB comprised between 1 and 8, and (iii) mixing said ingredients in an appropriate container. The compositions of the invention may be prepared in advance and stored in any appropriate container (flask, bottle, etc.). Alternatively, the compositions may be prepared extemporaneously, e.g., by mixing the ingredients shortly before administration.

A further object of the invention is a kit comprising one or several containers as defined above.

Preferred Non-Human Animals Treated by Compositions of the Invention

The compositions of the present invention may be used for the treatment of any non-human animals, including porcine, ovine, bovine, canine, feline or avian and preferably livestock, breeding animals, avian animals, companion animals, and laboratory animals.

Livestock and breeding animals include non-human mammals such as cattle, horses, sheep, pigs, goats, camels, water buffalo, donkeys, rabbits, fallow deer, reindeer, and fur bearers such as minks, chinchillas, and raccoons.

Avian animals include, for example, chickens, hens, ducks, turkeys, guinea fowl, quail, geese, pigeons, parrots and ostriches, and bird species for keeping in domestic premises and in zoos.

Companion animals include, for example, horses, dogs and cats.

Laboratory animals and experimental animals include, for example, mice, rats, guinea pigs, and golden hamsters.

The compositions of the invention are particularly suited for treating pigs, ovines, bovines, horses, sheep, cattle, dogs, rabbits, or cats.

The compositions of the invention may be used in adults or young non-human animals, such as newborn to 10-day-old non-human animals.

Further aspects and advantages of the invention will be disclosed in the following illustrative experimental section.

EXAMPLES

A—Preparation of Compositions

The following compositions are prepared:

| Formula 1 | |
|---|---|
| Ingredient | g/100 mL |
| Toltrazuril | 3.5 |
| Iron (as gleptoferron) | 18.3 |
| Water | Qs |

| Formula 2 | |
|---|---|
| Ingredient | g/100 mL |
| Sorbitan monooleate | 0.3 |
| Toltrazuril | 3.5 |
| Iron (as gleptoferron) | 19.4 |
| Water | Qs |

| Formula 3 | |
|---|---|
| Ingredient | g/100 mL |
| Sorbitan monooleate | 0.3 |
| Diethylene glycol monoethyl ether | 10 |
| Toltrazuril | 3.5 |
| Iron (as gleptoferron) | 17.8 |
| Water | Qs |

| Formula 4 | |
|---|---|
| Ingredient | g/100 mL |
| Sorbitan monooleate | 0.3 |
| Diethylene glycol monoethyl ether | 10 |
| Copolymer Polyoxyl 35—hydrogenated castor oil | 0.1 |
| Toltrazuril | 3.5 |
| Iron (as gleptoferron) | 17.8 |
| Water | Qs |

| Formula 5 | |
|---|---|
| Ingredient | g/100 mL |
| Sorbitan monooleate | 0.3 |
| Copolymer Polyoxyl 35—hydrogenated castor oil | 0.1 |
| Toltrazuril | 3.5 |
| Iron (as gleptoferron) | 19.4 |
| Water | Qs |

| Formula 6 | |
|---|---|
| Ingredient | g/100 mL |
| Sorbitan monooleate | 0.1 |
| Sodium chloride | 1.0 |
| Diethylene glycol monoethyl ether | 10 |
| Toltrazuril | 3.5 |
| Iron (as gleptoferron) | 17.8 |
| Water | Qs |

| Formula 7 | |
|---|---|
| Ingredient | g/100 mL |
| Propylene glycol monolaurate | 0.3 |
| Sodium chloride | 1.0 |
| Copolymer Polyoxyl 35—hydrogenated castor oil | 0.1 |
| Toltrazuril | 3.5 |
| Iron (as gleptoferron) | 19.3 |
| Water | Qs |

| Formula 8 | |
|---|---|
| Ingredient | g/100 mL |
| Sorbitan monooleate | 0.3 |
| Copolymer Polyoxyl 35—hydrogenated castor oil | 0.1 |
| Toltrazuril | 3.5 |
| Iron (as dextran) | 19.4 |
| Water | Qs |

| Formula 9 | |
|---|---|
| Ingredient | g/100 mL |
| Sodium docusate | 0.1 |
| Silicone emulsion | 0.1 |
| Sodium chloride | 1.5 |
| Iron (as gleptoferron) | 13.5 |
| Toltrazuril | 4.2 |
| Water | qs |

Formula 10

| Ingredient | g/100 mL |
|---|---|
| Sodium docusate | 0.1 |
| Silicone emulsion | 0.1 |
| Sodium chloride | 1.0 |
| Diethylene glycol monoethyl ether | 5.0 |
| Iron (as gleptoferron) | 13.5 |
| Toltrazuril | 4.2 |
| Water | qs |

Formula 11

| Ingredient | g/100 mL |
|---|---|
| Sodium docusate | 0.2 |
| Simethicone emulsion | 0.1 |
| Sodium chloride | 0.5 |
| Povidone | 1.0 |
| Colloidal silicon dioxide | 0.5 |
| Phenol | 0.6 |
| Iron (as gleptoferron) | 13.5 |
| Toltrazuril | 4.2 |
| Water | QS |

Formula 12

| Ingredient | g/100 mL |
|---|---|
| Sodium docusate | 0.2 |
| Simethicone emulsion | 0.1 |
| Sodium chloride | 1.0 |
| Povidone | 1.0 |
| Colloidal silicon dioxide | 0.5 |
| Phenol | 0.6 |
| Iron (as gleptoferron) | 13.5 |
| Toltrazuril | 4.2 |
| Water | QS |

Formula 13

| Ingredient | g/100 mL |
|---|---|
| Sodium docusate | 0.1 |
| Simethicone emulsion | 0.1 |
| Sodium chloride | 1.0 |
| Povidone | 1.0 |
| Colloidal silicon dioxide | 0.5 |
| Phenol | 0.6 |
| Iron (as gleptoferron) | 13.5 |
| Toltrazuril | 4.2 |
| Water | QS |

Formula 14

| Ingredient | g/100 mL |
|---|---|
| Sodium docusate | 0.1 |
| Simethicone emulsion | 0.1 |
| Sodium chloride | 1.0 |
| Povidone | 1.0 |
| Colloidal silicon dioxide | 0.5 |
| Phenol | 0.6 |
| Iron (as gleptoferron) | 18.8 |
| Toltrazuril | 2.9 |
| Water | QS |

B—Evaluation of the Foaming Properties of the Compositions

The foaming aspect of the formulations is estimated according to the following procedure:
Filling of graduated test tube with 7 g of product.
Vigorous agitation of the test tube for 45 seconds.
Measuring of the foam formed at the following time intervals:
right after agitation,
1 minute after agitation,
3 minutes after agitation,
5 minutes after agitation, and
10 minutes after agitation.
The results are presented in the following table.

| Time | Formula | | | | | | | | | | | | | |
|---|---|---|---|---|---|---|---|---|---|---|---|---|---|---|
| | 1 | 2 | 3 | 4 | 5 | 6 | 7 | 8 | 9 | 10 | 11 | 12 | 13 | 14 |
| | Foam height (mm) | | | | | | | | | | | | | |
| 0 min | 32 | 3 | 2.5 | 2 | 3 | 2 | 4 | 3 | 15 | 15 | 20 | 19 | 20 | 6 |
| 1 min | 34 | 3 | 2 | 2 | 2 | 2 | 1 | 2 | 1 | 0 | 17 | 17 | 9 | 4 |
| 3 min | 34 | 3 | 1.5 | 1.5 | 2 | 2 | 1 | 2 | 0 | 0 | 15 | 2 | 3 | 2 |
| 5 min | 33 | 3 | 1 | 1 | 1.5 | 2 | 1 | 2 | 0 | 0 | 5 | 1 | 2 | 2 |
| 10 min | 33 | 2.5 | 0.5 | 0.5 | 1 | 1 | 0 | 2 | 0 | 0 | 1 | 0 | 0 | 0 |

Formula 1, which does not contain a low HLB surfactant according to the invention, exhibits high foaming 10 minutes after agitation. In contrast, Formulae 2 to 8 have a foam height below 3 mm after 10 minutes, and therefore have remarkable antifoaming properties.

Formulae 3, 4, 7 and 11 to 14 are remarkable since they are characterized by a rapid decrease of the foam thickness, which almost disappeared 10 minutes post-agitation.

Formulae 9 and 10 are particularly remarkable since they are characterized by a very fast decrease of the foam thickness, which almost disappeared 1 to 3 minutes post-agitation The formation of foam when reconstituting liquid dosage formulations is undesirable and disruptive. The remarkable capacity of the formulations of the invention to avoid and/or quickly stop formation of foam in an aqueous suspension after reconstitution is therefore particularly advantageous since it allows the user to quickly syringe the suspension in optimal conditions, to secure the toltrazuril and iron dose taken, and to minimize the phenomenon of resuspension observed after agitation.

We claim:

1. A method for treating coccidiosis in a non-human animal comprising administering to said animal a composition comprising: at least one triazine compound selected from diclazuril and/or toltrazuril; an iron complex comprising an aqueous colloidal solution of beta-ferric oxyhydroxide and dextran glucoheptonic acid; at least one high HLB surfactant; and a silicone emulsion, a simethicone emulsion or a combination of a silicone emulsion and a simethicone emulsion, said emulsions having a Hydrophilic-Lipophilic Balance (HLB) of between 1 and 8.

2. The method according to claim 1, wherein the non-human animal is swine.

3. The method according to claim 2, wherein said swine is a piglet.

4. The method according to claim 1, wherein the composition is administered by intramuscular injection.

5. The method according to claim 1, wherein the composition is administered by subcutaneous, intradermal or intravenous injection.

6. The method according to claim 1, said composition further comprising at least one hydrophilic solvent and/or at least one salt and/or at least one thickening agent and/or at least one preservative.

7. The method according to claim 1, wherein said composition comprises:
from 1% to 10% by weight of the at least one triazine compound,
from 10% to 25% by weight of the iron complex,
from 0.01% to 5% by weight of a silicone emulsion, a simethicone emulsion, or a combination of a silicone emulsion and a simethicone emulsion, said emulsions having an HLB of between 1 and 8,
from 0% to 30% by weight of one or more hydrophilic solvent(s),
from 0% to 10% by weight of one or more salt(s),
from 0.05% to 5% by weight of the at least one high HLB surfactant,
from 0% to 10% by weight of one or more thickening agent(s), and
from 0% to 10% by weight of one or more preservative(s),
with respect to the total weight of the composition.

8. The method according to claim 1, wherein said composition comprises toltrazuril and diclazuril.

9. The method according to claim 1, wherein said composition comprises toltrazuril.

10. The method according to claim 1, wherein said composition comprises a simethicone emulsion.

11. The method according to claim 10, wherein the simethicone emulsion comprises about 25 to 35% by weight of simethicone USP.

12. The method according to claim 10, wherein the simethicone emulsion comprises polydimethylsiloxane, octamethylcyclotetrasiloxane, methylcellulose, decamethylcyclopentasiloxane, methylated silica and sorbic acid.

13. The method according to claim 1, said composition further comprising a pharmaceutically acceptable carrier or excipient.

14. The method according to claim 1, wherein said at least one triazine compound is diclazuril.

15. The method according to claim 7, said at least one high HLB surfactant having a HLB greater than 8.

16. The method according to claim 7, said composition comprising 0.05% to 1% by weight of said at least one high HLB surfactant, said at least one high HLB surfactant having an HLB greater than 8.

17. The method according to claim 1, said composition further comprising a salt.

18. The method according to claim 17, said composition comprising a salt in an amount of 0.1% to 10% by weight of the composition.

19. The method according to claim 7, wherein said at least one high HLB surfactant is a polyethylene castor oil derivative, polyoxyethylene alkyl ether, polyoxyethylene sorbitan fatty acid ester, polyoxyethylene stearate, sodium lauryl sulfate, sodium docusate, cetrimide, phospholipids, or cetylpyridinium chloride.

20. The method according to claim 19, wherein the at least one high HLB surfactant is sodium docusate.

21. The method according to claim 19, said composition comprising toltrazuril, an iron complex comprising an aqueous colloidal solution of beta-ferric oxyhydroxide and dextran glucoheptonic acid, a simethicone emulsion having a Hydrophilic-Lipophilic Balance (HLB) of between 1 and 8, and a high HLB surfactant having an HLB greater than 8.

22. The method according to claim 21, wherein the high HLB surfactant is sodium docusate.

23. The method according to claim 21, said composition further comprising a thickening agent.

24. The method according to claim 23, wherein the thickening agent is colloidal silicone dioxide and povidone.

25. The method according to claim 21, wherein the composition comprises a mixture of colloidal silicone dioxide and povidone as a thickening agent and sodium docusate as the high HLB surfactant.

26. A method for treating coccidiosis in a non-human animal comprising administering to said animal a composition comprising:
at least one triazine compound selected from diclazuril and/or toltrazuril;
an iron complex comprising an aqueous colloidal solution of beta-ferric oxyhydroxide and dextran glucoheptonic acid;
a simethicone emulsion having a Hydrophilic-Lipophilic Balance (HLB) of between 1 and 8;
sodium docusate;
a mixture of colloidal silicone dioxide and povidone; and
a salt.

27. The method according to claim 26, wherein the salt is sodium chloride.

* * * * *